United States Patent [19]

Shimizu et al.

[11] Patent Number: 4,931,561

[45] Date of Patent: Jun. 5, 1990

[54] PROCESS FOR PREPARING NITRILES

[75] Inventors: Shinkichi Shimizu, Hirakata; Takayuki Shoji, Osaka; Kanji Kono, Osaka; Toru Nakaishi, Osaka, all of Japan

[73] Assignee: Koei Chemical Co., Ltd., Osaka, Japan

[21] Appl. No.: 224,012

[22] Filed: Jul. 25, 1988

[30] Foreign Application Priority Data

Jul. 29, 1987 [JP] Japan ................ 62-189168
Jul. 29, 1987 [JP] Japan ................ 62-189169
Jul. 29, 1987 [JP] Japan ................ 62-189170

[51] Int. Cl.$^5$ ................ C07D 241/14; C07D 213/84; C07D 213/85
[52] U.S. Cl. ................ 544/336; 546/286; 546/287
[58] Field of Search ................ 544/336; 546/286, 287

[56] References Cited

U.S. PATENT DOCUMENTS

| | | | |
|---|---|---|---|
| 2,294,130 | 8/1942 | Porter | 549/248 |
| 3,970,659 | 7/1976 | Elion et al. | 546/286 |
| 4,336,205 | 6/1982 | Onishi et al. | 546/286 |
| 4,603,207 | 7/1986 | DiCosimo et al. | 546/286 |
| 4,778,890 | 10/1988 | Shimizu et al. | 546/286 |

FOREIGN PATENT DOCUMENTS 483155 5/1952 Canada ................ 546/286

Primary Examiner—Mukund J. Shah
Assistant Examiner—E. Bernhardt
Attorney, Agent, or Firm—Wenderoth, Lind and Ponack

[57] ABSTRACT

A heteroaromatic nitrile is prepared in high conversion and yield by catalytically reacting an alkyl-substituted heteroaromatic compound with molecular oxygen and ammonia in the presence of a catalyst having the following composition:

$$Mo(P)_x(A)_y(B)_z(O)_w \qquad (I)$$

wherein x, y, z and w represent atomic ratios of phosphorus, an element A defined below, an element B defined below and oxygen to molybdenum, respectively and (i) x and z are both 0 (zero), y is from 0.1 to 5, and A is at least one element selected from the group consisting of cerium and tungsten, or (ii) x is from 0.1 to 7, y is from 0 to 5, z is from 0 to 5, A is at least one element selected from the group consisting of cerium, manganese and tungsten, and B is at least one element selected from the group consisting of thallium, titanium, niobium and aluminum, or (iii) x is from 0.5 to 7, y is from 0 to 5, z is from 0.01 to 2. A is at least one element selected from the group consisting of cerium, manganese and tungsten, and B is vanadium, and w is defined from the valencies of molybdenum, phosphorus, the element A, the element B and the values x, y and z.

5 Claims, No Drawings

PROCESS FOR PREPARING NITRILES

BACKGROUND OF THE INVENTION

1. Field of the Invention

The present invention relates to a process for preparing nitriles. More particularly, it relates to a process for producing a heteroaromatic nitrile comprising catalytically reacting an alkyl-substituted heteroaromatic compound with ammonia and molecular oxygen in a gaseous phase (namely, by ammoxidation).

The heteroaromatic nitriles are useful as starting materials in the preparation of medicines or agricultural chemicals.

2. Description of the Related Art

Japanese Patent Publication No. 19706/1982 and Japanese Patent Kokai Publication No. 156039/1982 disclose, as a catalyst for ammoxidation, a catalyst comprising antimony oxide, vanadium oxide and an oxide of a metal selected from the group consisting of iron, copper, titanium, cobalt, manganese and nickel. Although this catalyst has a comparatively high selectivity in case of a monoalkyl-substituted heteroaromatic compound, it tends to induce unfavorable reactions such as cleavage of a heteroaromatic ring in case of a dialkyl-substituted heteroaromatic compound so that the selectivity of the desired nitriles is decreased. In addition, this catalyst suffers from decrease of catalytic activity through reduction with ammonia and further its catalytic activity is largely decreased by deposition of carbon.

SUMMARY OF THE INVENTION

As a result of extensive study, it has been found that, in the preparation of the heteroaromatic nitriles by ammoxidation of the alkyl-substituted heteroaromatic compounds, the unfavorable reactions such as the cleavage of heteroaromatic rings or dealkylation can be suppressed and the heteroaromatic nitriles can be prepared with high selectivity even in case of the dialkyl-substituted heteroaromatic compounds when a molybdenum oxide base compound having a specific composition is used as a catalyst. It has also been found that said compound has good resistance against heat and reduction.

According to the present invention, there is provided a process for preparing a heteroaromatic nitrile comprising catalytically reacting an alkyl-substituted heteroaromatic compound with molecular oxygen and ammonia in the presence of a catalyst having the following composition:

$$Mo(P)_x(A)_y(B)_z(O)_w \qquad (I)$$

wherein x, y, z and w represent atomic ratios of phosphorus, an element A defined below, an element B defined below and oxygen to molybdenum, respectively and (i) x and z are both 0 (zero), y is from 0.1 to 5, and A is at least one element selected from the group consisting of cerium and tungsten, or (ii) x is from 0.1 to 7, y is from 0 to 5, z is from 0 to 5, A is at least one element selected from the group consisting of cerium, manganese and tungsten, and B is at least one element selected from the group consisting of thallium, titanium, niobium and aluminum, or (iii) x is from 0.5 to 7, y is from 0 to 5, z is from 0.01 to 2, A is at least one element selected from the group consisting of cerium, manganese and tungsten, and B is vanadium, and w is defined from the valencies of molybdenum, phosphorus, the element A, the element B and the values x, y and z.

DETAILED DESCRIPTION OF THE INVENTION

The catalyst having the composition (I) may be prepared by any of conventional processes for preparing an oxide type catalyst. For example, compounds of the constituent elements of the catalyst are reacted in an aqueous solution, the resulting reaction mixture is evaporated to dryness and the dried product is calcined to obtain the catalyst. The calcination temperature is preferably from 350 to 700° C. The kind of the compound of each element is not limited and any of conventionally used compounds may be used in the preparation of the catalyst.

Specific examples of the molybdenum compound are ammonium molybdate, ammonium paramolybdate, molybdenum trioxide, molybdenum pentachloride and the like.

Specific examples of the phosphate compound are phosphoric acid, metaphosphoric acid, phosphorous acid, phosphates (e.g. ammonium phosphate, etc.) and the like.

Specific examples of the cerium compound are metallic cerium, cerium oxide, cerium nitrate, cerium hydroxide, cerium chloride, cerium carbonate, cerium sulfate and the like.

Specific examples of the manganese compound are metallic manganese, manganese oxide, manganese nitrate, manganese hydroxide, manganese chloride, manganese carbonate, manganese sulfate and the like.

Specific examples of the tungsten compound are ammonium tungstate, tungsten trioxide and the like.

Specific examples of the thallium compound are metallic thallium, thallium nitrate, thallium hydroxide, thallium chloride, thallium carbonate, thallium sulfate and the like.

Specific examples of the titanium compound are metallic titanium, titanium oxide and the like.

Specific examples of the niobium compound are metallic niobium, niobium oxide, niobic acid and the like.

Specific examples of the aluminum compound are metallic aluminum, aluminum oxide, aluminum nitrate, aluminum hydroxide, aluminum chloride, aluminum sulfate and the like.

Specific examples of the vanadium compound are ammonium metavanadate, vanadium pentoxide and the like.

The catalyst used according to the present invention may be supported on a catalyst carrier such as silica, α-alumina, γ-alumina, silicon carbide, titanium oxide, diatomaceous earth and zeolite. Among them, α-alumina and silicon carbide are preferred.

The alkyl-substituted heteroaromatic compound to be converted to the heteroaromatic nitrile according to the present invention includes mono-, di- or trialkyl-substituted pyridines, mono-, di- or trialkyl-substituted pyrazines and the like. Specific examples of the alkyl-substituted pyridine are 2-methylpyridine, 3-methylpyridine, 4-methylpyridine, 2,3-dimethylpyridine, 2,4-dimethylpyridine, 2,5-dimethylpyridine, 2,6-dimethylpyridine, 3,4-dimethylpyridine, 3,5-dimethylpyridine, 2-methyl-5-ethylpyridine, 2,4,6-trimethylpyridine, 2,3,4-trimethylpyridine, 2,3,5-trimethylpyridine, 2,3,6-trimethylpyridine and the like. Specific examples of the alkyl-substituted pyrazine are methylpyrazine, ethylpyrazine, 2,3-dimethylpyrazine, 2,5-dimethylpyrazine, 2,6-dimethylpyrazine, 2-methyl-5-ethylpyrazine, 2-methyl-6-ethylpyrazine and the like.

The concentration of the alkyl-substituted heteroaromatic compound in the gaseous reaction mixture may be from 0.15 to 10% by mole. In the reaction mixture, the molar ratio of the alkyl-substituted heteroaromatic compound, ammonia and molecular oxygen is not critical and preferably is in a range of 1:1–100:1.5–20.

As molecular oxygen, air is preferably used although pure oxygen or a mixture of pure oxygen and air may be used.

The gaseous reaction mixture containing the alkyl-substituted heteroaromatic compound, molecular oxygen and ammonia may be diluted with an inactive gas such as steam or nitrogen.

In the process according to the present invention, the reaction temperature is from 300 to 650° C., preferably from 350 to 600° C. The space velocity is from 200 to 10,000 hr$^{-1}$, preferably from 300 to 5,000 hr$^{-1}$. Usually, the reaction according to the present invention is carried out under atmospheric pressure, although it may be carried out under reduced or high pressure. The reaction of the present invention is generally performed with a fixed bed reactor, although it may be performed with a fluidized bed reactor.

The present invention will be hereinafter explained further in detail by the following examples, in which conversion and yield are calculated by the following equations: Conversion (%) = 100 x Conversion (%) = 100 ×

$$\frac{\text{Reacted alkyl-substituted heteroaromatic compound (mole)}}{\text{Supplied alkyl-substituted heteroaromatic compound (mole)}}$$

Yield (%) = 100 ×

$$\frac{\text{Produced nitrile compound (mole)}}{\text{Supplied alkyl-substituted heteroaromatic compound (mole)}}$$

Example 1

In distilled water (300 g), ammonium paramolybdate (50 g), cerium nitrate (47 g) and 67.5% nitric acid (26 g) were added and reacted for 2 hours at 80° C. while stirring. The reaction mixture was concentrated and dried followed by calcination at 550° C. for 5 hours in the air. The resulting catalyst had a composition: $Mo_2Ce_1O_8$ ($MoCe_{0.5}O_4$). The catalyst (10 cc) was filled in a reactor tube having a diameter of 12.6 mm. With heating the catalyst filled portion of the reactor at 400° C., a gaseous mixture of 2,5-dimethylpyrazine, ammonia, air and steam in a molar ratio of 1:20:10:5 was flowed through the reactor at a space velocity of 900 hr$^{-1}$, and the reacted gaseous mixture was trapped by water for 20 minutes, after 10 minutes, 1 hour or 10 hours from the start of the reaction and analyzed by gas chromatography. The results of the analysis are shown in Table 1.

Comparative Example

According to the procedures of Example 1 of Japanese Patent Kokai Publication No. 156039/1982, a catalyst of the formula: $Sb_4V_1Ti_4Si_7O_{30.5}$ was prepared, and in the same manner as in Example 1 of the present invention, 2,5-dimethylpyrazine was ammoxidized at 380° C. The results are shown in Table 1.

Example 2

In the same manner as in Example 1, a catalyst having the composition: $Mo_{1.5}W_1O_{7.5}$ was prepared and 2,5-dimethylpyrazine was ammoxidized in the same manner as in Example 1 but heating the catalyst filled portion of the reactor at 440° C. The results are shown in Table 1.

TABLE 1

| Example No. | Starting time of trapping | Conversion (%) | 5-Methyl-2-cyano-pyrazine yield (%) | 2,5-Dicyano-pyrazine yield (%) | 2-Cyano-pyrazine yield (%) |
|---|---|---|---|---|---|
| 1 | 10 min. | 40.9 | 24.2 | 10.8 | 0.9 |
|  | 1 hr. | 41.0 | 24.6 | 10.6 | 0.8 |
|  | 100 hrs. | 41.2 | 24.5 | 10.3 | 0.8 |
| Comparative | 10 min. | 37.6 | 18.1 | 11.3 | 1.3 |
|  | 1 hr. | 16.2 | 5.4 | 4.3 | 0.0 |
| 2 | 1 hr. | 51.5 | 25.1 | 18.1 | 1.1 |

Example 3

In distilled water (300 g), ammonium paramolybdate (80 g) and 85% phosphoric acid (52 g) were added and reacted for 2 hours at 90° C. while stirring. The reaction mixture was concentrated and dried followed by calcination at 550° C. for 5 hours in the air. The resulting catalyst had a composition: $Mo_1P_1O_{5.5}$. The catalyst (10 cc) was filled in the same reactor tube as used in Example 1. With heating the catalyst filled portion of the reactor at 430° C., a gaseous mixture of 2,5-dimethylpyrazine, ammonia, air and steam in a molar ratio of 1:20:10:5 was flowed through the reactor at a space velocity of 860 hr$^{-1}$, and the reacted gaseous mixture was trapped by water for 20 minutes, after 10 minutes, 1 hour or 100 hours from the start of the reaction and analyzed by gas chromatography. The results of the analysis are shown in Table 2.

TABLE 2

| Example No. | Starting time of trapping | Conversion (%) | 5-Methyl-2-cyano-pyrazine yield (%) | 2,5-Dicyano-pyrazine yield (%) | 2-Cyano-pyrazine yield (%) |
|---|---|---|---|---|---|
| 3 | 10 min. | 35.1 | 27.1 | 4.8 | 0.5 |
|  | 1 hr. | 36.1 | 27.6 | 4.9 | 0.5 |
|  | 100 hrs. | 34.8 | 26.9 | 5.0 | 0.4 |

Examples 4 to 10

2,5-Dimethylpyrazine was ammoxidized in the presence of a catalyst shown in Table 3 under reaction conditions shown in Table 3. The reacted gaseous mixture was trapped by water for 20 minutes, after one hour from the start of the reaction and analyzed by gas chromatography. The results of the analysis are shown in Table 3.

TABLE 3

| Example No. | Catalyst composition | Reaction temperature (°C.) | SV (Hr$^{-1}$) | 2,5-Dimethyl-pyrazine/ammonia/air/steam (molar ratio) | Conversion (%) | 5-Methyl-2-cyano-pyrazine yield (%) | 2,5-Dicyano-pyrazine yield (%) | 2-Cyano-pyrazine yield (%) |
|---|---|---|---|---|---|---|---|---|
| 4 | $Mo_2P_3Ce_1O_{15}$ | 380 | 1,090 | 1/20/10/5 | 34.9 | 27.6 | 2.9 | 0.4 |
| 5 | $Mo_2P_3Mn_1O_{14.5}$ | 440 | 1,050 | 1/20/10/5 | 57.9 | 39.5 | 10.1 | 0.4 |
| 6 | $Mo_{2.5}P_4W_1Ce_{0.3}O_{21.1}$ | 450 | 1,100 | 1/20/10/5 | 67.8 | 37.1 | 23.1 | 0.3 |
| 7 | $Mo_2P_3W_1Tl_{0.1}O_{16.55}$ | 440 | 1,100 | 1/20/10/5 | 67.6 | 38.9 | 15.8 | 0.1 |
| 8 | $Mo_2P_3W_1Ti_{0.3}O_{17.1}$ | 440 | 1,300 | 1/5/20/15 | 65.8 | 40.5 | 20.2 | 0.0 |
| 9 | $Mo_2P_3W_1Nb_{0.1}O_{16.75}$ | 420 | 1,300 | 1/5/20/16 | 67.9 | 44.0 | 16.7 | 0.0 |
| 10 | $Mo_2P_3W_1Al_{1.5}O_{18.75}$ | 440 | 1,000 | 1/5/20/10 | 54.3 | 43.7 | 5.3 | 0.2 |

Example 11

In the same manner as in Example 3 but using the catalyst as used in Example 10 and charging methylpyrazine, ammonia, air and steam in a molar ratio of 1:20:15:5, the ammoxidation was carried out and the reacted gaseous mixture was trapped by water for 20 minutes, after one hour from the start of the reaction and analyzed by gas chromatography. The conversion was 86.9% and the yield of cyanopyrazine was 66.8 %.

Examples 12 to 15

2,6-Dimethylpyridine was ammoxidized in the presence of a catalyst shown in Table 4 under reaction conditions shown in Table 4. The reacted gaseous mixture was trapped by water for 20 minutes, after one hour from the start of the reaction and analyzed by gas chromatography. The results of the analysis are shown in Table 4.

TABLE 4

| Example No. | Catalyst composition | Reaction temperature (°C.) | SV (Hr$^{-1}$) | 2,6-Dimethyl-pyridine/ammonia/air (molar ratio) | Conversion (%) | 6-Methyl-2-cyano-pyridine yield (%) | 2,6-Dicyano-pyridine yield (%) | 2-Cyano-pyridine yield (%) |
|---|---|---|---|---|---|---|---|---|
| 12 | $Mo_2P_3W_1O_{16.5}$ | 450 | 910 | 1/40/40 | 95.1 | 55.3 | 21.9 | 0.7 |
| 13 | $Mo_{2.5}P_4W_1Ce_{0.3}O_{21.1}$ | 450 | 780 | 1/40/40 | 79.1 | 47.0 | 11.9 | 0.5 |
| 14 | $Mo_2P_3W_1Al_{1.5}O_{18.75}$ | 450 | 890 | 1/40/40 | 97.5 | 69.0 | 17.9 | 0.5 |
| 15 | $Mo_2P_3W_1Nb_{0.3}O_{12.25}$ | 420 | 1,400 | 1/40/40 | 95.1 | 75.3 | 12.7 | 0.6 |

Example 16

In distilled water (300 g), ammonium paramolybdate (50 g), 85% phosphoric acid (49 g) and vanadium pentaoxide (13 g) were added and reacted for 1 (one) hour at 90° C. while stirring. The reaction mixture was concentrated and dried followed by calcination at 550° C. for 5 hours in the air. The resulting catalyst had a composition: $Mo_2V_1P_3O_{16}$. The catalyst (10 cc) was filled in the same reactor tube as used in Example 1. With heating the catalyst filled portion of the reactor at 420° C., a gaseous mixture of 2,5-dimethylpyrazine, ammonia, air and steam in a molar ratio of 1:20: 10:5 was flowed through the reactor at a space velocity of 880 hr$^{-1}$, and the reacted gaseous mixture was trapped by water for 20 minutes, after 10 minutes, 1 hour or 10 hours from the start of the reaction and analyzed by gas chromatography. The results of the analysis are shown in Table 5.

TABLE 5

| Example No. | Starting time of trapping | Conversion (%) | 5-Methyl-2-cyano-pyrazine yield (%) | 2,5-Dicyano-pyrazine yield (%) | 2-Cyano-pyrazine yield (%) |
|---|---|---|---|---|---|
| 16 | 10 min. | 32.1 | 21.1 | 5.0 | 0.5 |
|  | 1 hr. | 32.8 | 22.4 | 6.0 | 0.5 |
|  | 100 hrs. | 31.9 | 21.8 | 5.8 | 0.5 |

Examples 17 to 19

2,5-Dimethylpyrazine was ammoxidized in the presence of a catalyst shown in Table 6 under reaction conditions shown in Table 6. The reacted gaseous mixture was trapped by water for 20 minutes, after one hour from the start of the reaction and analyzed by gas chromatography. The results of the analysis are shown in Table 6.

Examples 20 and 21

2,6-Dimethylpyridine was ammoxidized in the presence of a catalyst shown in Table 4 under reaction conditions shown in Table 4. The reacted gaseous mixture was trapped by water for 20 minutes, after one hour from the start of the reaction and analyzed by gas chromatography. The results of the analysis are shown in Table 7.

TABLE 6

| Example No. | Catalyst composition | Reaction temperature (°C.) | SV (Hr$^{-1}$) | 2,5-Dimethyl pyrazine/ammonia/air/steam (molar ratio) | Conversion (%) | 5-Methyl-2-cyano-pyrazine yield (%) | 2,5-Dicyano-pyrazine yield (%) | 2-Cyano-pyrazine yield (%) |
|---|---|---|---|---|---|---|---|---|
| 17 | $Mo_2P_3V_1Ce_1O_{17.5}$ | 380 | 870 | 1/20/10/5 | 31.2 | 25.0 | 3.2 | 0.2 |
| 18 | $Mo_2P_3V_1W_1O_{19}$ | 450 | 840 | 1/20/10/5 | 43.3 | 27.2 | 8.1 | 0.3 |
| 19 | $Mo_2P_3V_1Mn_1O_{17}$ | 430 | 850 | 1/20/10/5 | 40.1 | 26.2 | 6.9 | 0.2 |

TABLE 7

| Example No. | Catalyst composition | Reaction temperature (°C.) | SV (Hr$^{-1}$) | 2,6-Dimethyl-pyridine/ammonia/air/steam (molar ratio) | Conversion (%) | 6-Methyl-2-cyano-pyridine yield (%) | 2,6-Dicyano-pyridine yield (%) | 2-Cyano-pyridine yield (%) |
|---|---|---|---|---|---|---|---|---|
| 20 | Mo$_1$P$_3$V$_1$W$_1$O$_{11.5}$ | 450 | 825 | 1/40/40/0 | 99.4 | 57.3 | 18.3 | 0.4 |
| 21 | Mo$_1$P$_3$V$_{0.3}$W$_2$O$_{17.25}$ | 440 | 1,050 | 1/50/50/1.6 | 100 | 16.3 | 52.8 | 0.8 |

What is claimed is:

1. A process for preparing a heteroaromatic nitrile comprising catalytically reacting an alkyl-substituted heteroaromatic compound selected from the group consisting of alkyl-substituted pyridines and alkyl-substituted pyrazines wherein the alkyl substituent is methyl or ethyl, with molecular oxygen and ammonia in the gaseous phase at a temperature of 300 to 650° C., in the presence of a catalyst having the following composition:

$$\mathrm{Mo(P)}_x(A)_y(B)_z(O)_w \qquad (I)$$

wherein x, y, z and w represent atomic ratios of phosphorus, an element A defined below, an element B defined below and oxygen to molybdenum, respectively and (i) x and z are both zero, y is from 0.1 to 5, and A is at least one element selected from the group consisting of cerium and tungsten, or (ii) x is from 0.1 to 7, y is from 0 to 5, z is from 0 to 5, A is at least one element selected from the group consisting of cerium, manganese and tungsten, and B is at least one element selected from the group consisting of thallium, titanium, niobium and aluminum, or (iii) x is from 0.5 to 7, y is a positive number up to 5, z is from 0.01 to 2, A is at least one element selected from the group consisting of cerium, managanese and tungsten, and B is vanadium, and w is defined from the valencies of molybdenum, phosphorus, the element A, the element B and the values x, y and z.

2. The process according to claim 1, wherein the alkyl-substituted pyridines are dialkyl-substituted pyridines.

3. The process according to claim 1, wherein the alkyl-substituted pyrazines are dialkyl-substituted pyrazines.

4. The process according to claim 1, wherein the catalyst is supported on a catalyst carrier.

5. The process according to claim 4, wherein the carrier is α-alumina or silicon carbide.

* * * * *